US00PP17065P2

(12) United States Plant Patent
Lommerse

(10) Patent No.: US PP17,065 P2
(45) Date of Patent: Aug. 29, 2006

(54) ***LOBELIA* PLANT NAMED 'KIELOWASKY'**

(50) Latin Name: *Lobelia×hybrida*
Varietal Denomination: Kielowasky

(75) Inventor: Henry Lommerse, Mariahout-Laarbeek (NL)

(73) Assignee: Kieft Bloemzaden B.V., Venhuizen (NL)

( * ) Notice: Subject to any disclaimer, the term of this patent is extended or adjusted under 35 U.S.C. 154(b) by 0 days.

(21) Appl. No.: 11/108,586

(22) Filed: Apr. 15, 2005

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
*Assistant Examiner*—Louanne Krawczewicz Myers
(74) *Attorney, Agent, or Firm*—C. A. Whealy

(57) ABSTRACT

A new and distinct cultivar of *Lobelia* plant named 'Kielowasky', characterized by its low-mounding and trailing plant habit; freely branching habit; dense and bushy plant form; vigorous growth habit; freely and continuous flowering habit; and intense violet blue-colored flowers.

1 Drawing Sheet

Botanical designation: *Lobelia×hybrida.*
Cultivar denomination: 'Kielowasky'.

BACKGROUND OF THE INVENTION

The present Invention relates to a new and distinct cultivar of *Lobelia* plant, botanically known as *Lobelia×hybrida*, and hereinafter referred to by the cultivar name Kielowasky.

The new *Lobelia* is a product of a planned breeding program conducted by the Inventor in Mariahout-Laarbeek, The Netherlands. The objective of the program is to create new trailing *Lobelia* cultivars that flower continuously during the flowering season.

The new *Lobelia* originated from a self-pollination made by the Inventor during the summer of 1998 of a proprietary selection of *Lobelia×hybrida* identified as code number KB-00-4/6, not patented. The new *Lobelia* was discovered and selected by the Inventor in a controlled environment in Mariahout-Laarbeek, The Netherlands, during the summer of 1999 from the resultant progeny of the above-mentioned self-pollination.

Asexual reproduction of the new cultivar by terminal cuttings since 2003 at Steenbergen, The Netherlands, has shown that the unique features of this new *Lobelia* are stable and reproduced true to type in successive generations.

SUMMARY OF THE INVENTION

Plants of the cultivar Kielowasky have not been observed under all possible environmental conditions. The phenotype may vary somewhat with variations in environment such as temperature and light intensity without, however, any variance in genotype.

The following traits have been repeatedly observed and are determined to be the unique characteristics of 'Kielowasky'. These characteristics in combination distinguish 'Kielowasky' as a new and distinct cultivar:

1. Low-mounding and trailing plant habit.
2. Freely branching habit; dense and bushy plant form.
3. Vigorous growth habit.
4. Freely and continuous flowering habit.
5. Intense violet blue-colored flowers.

Plants of the cultivar Kielowasky can be compared to plants of the parent selection. However in side-by-side comparisons conducted by the Inventor in Venhuizen, The Netherlands, plants of the new *Lobelia* and the parent selection differed in the following characteristics:

1. Plants of the new *Lobelia* were more freely flowering than plants of the parent selection.
2. Plants of the new *Lobelia* flowered for a longer period of time than plants of the parent selection.
3. Flower color of plants of the new *Lobelia* was more intense violet blue than flower color of plants of the parent selection.

Plants of the cultivar Kielowasky can also be compared to plants of the cultivar Wesstar, disclosed in U.S. Plant Pat. No. 12,678. However in side-by-side comparisons conducted by the Inventor in Venhuizen, The Netherlands, plants of the new *Lobelia* and the cultivar Wesstar differed in the following characteristics:

1. Plants of the new *Lobelia* were more freely flowering than plants of the cultivar Wesstar.
2. Plants of the new *Lobelia* flowered for a longer period of time than plants of the cultivar Wesstar.
3. Flower color of plants of the new *Lobelia* was more intense violet blue than flower color of plants of the cultivar Wesstar.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Lobelia.*

The photograph at the bottom of the sheet comprises a side perspective view of typical flowering plant of 'Kielowasky' grown in a container.

The photograph at the top left of the sheet is a close-up view of typical flowers and leaves of 'Kielowasky'.

The photograph at the top right of the sheet is a close-up view of a typical flower of 'Kielowasky'.

DETAILED BOTANICAL DESCRIPTION

Plants used in the aforementioned photographs and following description were grown under greenhouse conditions which closely approximate commercial production conditions during the spring and summer in Lompoc, Calif. Rooted young plants were grown in 10-cm containers in a polycarbonate-covered greenhouse and were about nine weeks from planting when the photographs and description were taken. During the production of the plants, day temperatures ranged from 21 to 24° C., night temperatures ranged from 16 to 18° C. and light levels ranged from 5,000 to 9,000 foot-candles. In the following description, color references are made to The Royal Horticultural Society Colour Chart, 1995 Edition, except where general terms of ordinary dictionary significance are used.

Botanical classification: *Lobelia×hybrida* cultivar Kielowasky.

Parentage: Self-pollination of a proprietary selection of *Lobelia×hybrida* identified as code number KB-00-4/6, not patented.

Propagation:

*Type cutting.*—Terminal vegetative cuttings.

*Time to initiate roots, summer.*—About 12 days at 21° C.

*Time to initiate roots, winter.*—About 16 days at 21° C.

*Time to produce a rooted young plant, summer.*—About 21 days at 21° C.

*Time to produce a rooted young plant, winter.*—About 28 days at 21° C.

*Root description.*—Fine, fibrous, and white in color.

*Rooting habit.*—Freely branching.

Plant description:

*Form.*—Low mounding and trailing flowering plants with intense violet blue-colored flowers. Lateral shoots outwardly spreading. Freely branching habit with about eight main branches with lateral branches forming at every node; dense and bushy. Vigorous growth habit.

*Plant height.*—About 12 cm.

*Plant diameter.*—About 26 cm.

*Lateral branch description.*—Length: About 22 cm. Diameter: About 1.5 mm. Internode length: About 4 cm. Cross-section: Squarish. Texture: Smooth, glabrous. Color: 147A.

*Foliage description.*—Arrangement: Alternate, simple; sessile. Length: About 3.5 cm. Width: About 8 mm. Shape: Narrowly elliptic. Apex: Acute. Base: Attenuate. Margin: Slightly serrate. Texture, upper and lower surfaces: Smooth, glabrous. Venation pattern: Pinnate, arcuate. Color: Developing foliage, upper and lower surfaces: 146A. Fully developed foliage, upper surface: 147A. Fully developed foliage, lower surface: 147B. Venation, upper surface: 147A. Venation, lower surface: 147B.

Flower description:

*Flower type and flowering habit.*—Single axillary flowers that are held outwardly. Flowers persistent. Flowering indeterminate. Freely and continuous flower habit; about 13 to 14 open flowers and flower buds per lateral branch. Flowers not fragrant.

*Flower shape.*—Petals fused at base; flowers tubular and bilaterally symmetrical with three larger lower petal lobes and two upright upper petal lobes.

*Natural flowering season.*—Late winter until frost in the autumn in The Netherlands.

*Flower longevity on the plant.*—Longevity of individual flowers is highly dependent on weather conditions; typically about five to seven days.

*Flower size.*—Diameter: About 1.5 cm. Depth (height): About 1.8 cm. Flower length (tube and lobes): About 1.8 cm. Tube length: About 1.4 cm. Throat diameter, distal end: About 3 mm. Tube diameter, proximal end: About 2 mm.

*Flower buds.*—Length: About 1.4 cm. Diameter: About 4 mm. Shape: Roughly obovate. Color: More gray than 97A.

*Petal lobes.*—Arrangement: Single whorl of five petals, fused; three larger lower petal lobes and two smaller upper petal lobes. Length, upper lobes: About 5 mm. Length, lower lobes: About 9 mm. Width, upper lobes: About 1 mm. Width, lower lobes: About 6 mm. Shape, upper and lower lobes: Elliptic. Apex, upper and lower lobes: Broadly acute to rounded. Margin, upper and lower lobes: Entire. Texture, upper and lower lobes, upper and lower surfaces: Smooth, glabrous; velvety. Color: Developing flowers, upper surface: 96B. Developing flowers, lower surface: 96D. Fully developed flowers, upper surface: 96C; color becoming closer to 97A with the development. Fully developed flowers, lower surface: 97B. Throat: 155D; three spots at base of lower lobes, 96A. Tube: 155D.

*Sepals.*—Arrangement: Single whorl of five sepals, fused at base; star-shaped calyx. Length: About 1 cm. Width: About 1 mm. Shape: Linear. Apex: Acute. Margin: Entire. Texture, upper and lower surfaces: Smooth, glabrous. Color, upper and lower surfaces: 146A.

*Peduncles.*—Strength: Flexible and wiry, flowers held outwardly. Length: About 2.8 cm. Diameter: Less than 1 mm. Angle: About 45° from vertical. Color: 146A.

*Reproductive organs.*—Stamens: Quantity per flower/arrangement: About five, anthers appressed to style. Anther length: About 2 mm. Anther color: 202B. Pollen amount: Scarce. Pollen color: 158A. Pistils: Quantity per flower: One. Pistil length: About 1 cm. Stigma shape: Rounded. Stigma color: 94B. Style length: About 7 mm. Style color: 145B. Ovary color: 145A.

*Seed/fruit.*—Seed and fruit production have not been observed.

Disease/pest resistance: Plants of the new *Lobelia* have not been noted to be resistant to pathogens and pests common to *Lobelia*.

Weather tolerance: Plants of the new *Lobelia* have exhibited good tolerance to rain and wind and to tolerate temperatures from 4 to about 30° C.

It is claimed:

1. A new and distinct cultivar of *Lobelia* plant named 'Kielowasky', as illustrated and described.

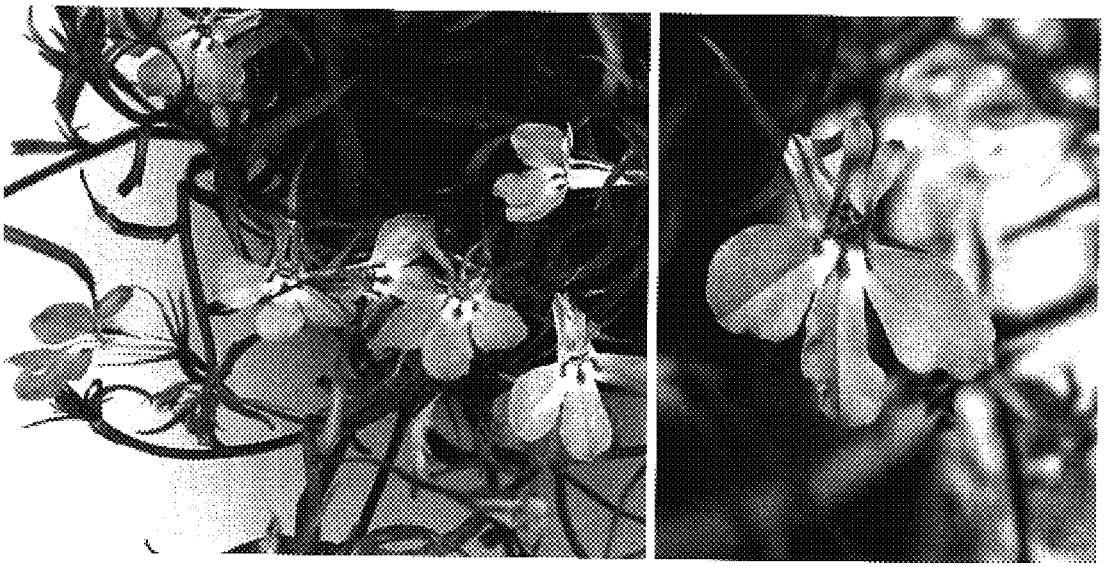
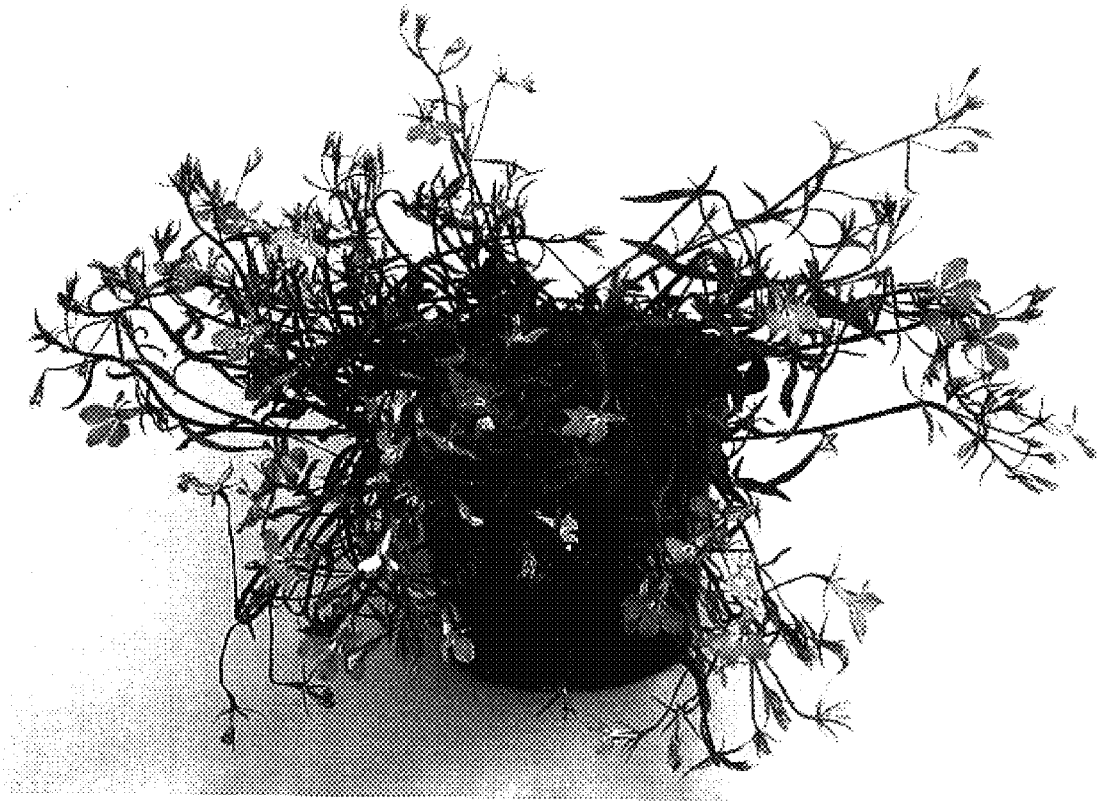

* * * * *